United States Patent [19]

Stevenson, Jr.

[11] 4,176,032
[45] Nov. 27, 1979

[54] CHLORINE DIOXIDE ANALYZER
[75] Inventor: Roberts G. Stevenson, Jr., New Britain, Pa.
[73] Assignee: Fischer & Porter Co., Warminster, Pa.
[21] Appl. No.: 883,284
[22] Filed: Mar. 3, 1978
[51] Int. Cl.$^2$ ............................................. G01N 27/46
[52] U.S. Cl. ................................. 204/195 P; 204/1 T
[58] Field of Search ............................ 204/1 B, 195 P
[56] References Cited
U.S. PATENT DOCUMENTS

| 3,235,477 | 2/1966  | Keyser et al.   | 204/195 P |
| 3,528,403 | 9/1970  | Imredy          | 204/195 P |
| 3,794,575 | 2/1974  | Niedrach et al. | 204/195 P |
| 3,839,178 | 10/1974 | Macur           | 204/195 P |
| 3,948,746 | 4/1976  | Poole           | 204/195 P |

Primary Examiner—T. Tung
Attorney, Agent, or Firm—Michael Ebert

[57] ABSTRACT

A system adapted to continuously and accurately measure the concentration of chlorine dioxide dissolved in liquid, the system including a sensor immersible in the liquid being tested. The sensor is constituted by a noble-metal measuring electrode, an oxidizable-metal counter electrode and an electrolyte which together define an electrochemical cell whose output current depends on the amount of chlorine dioxide passing into the cell through a diffusion membrane permeable to chlorine dioxide but not to the liquid. The chlorine dioxide within the cell is electrochemically reduced at the surface of the measuring electrode to generate a current proportional to its concentration, the counter-electrode being oxidized to complete the cell reaction.

9 Claims, 6 Drawing Figures

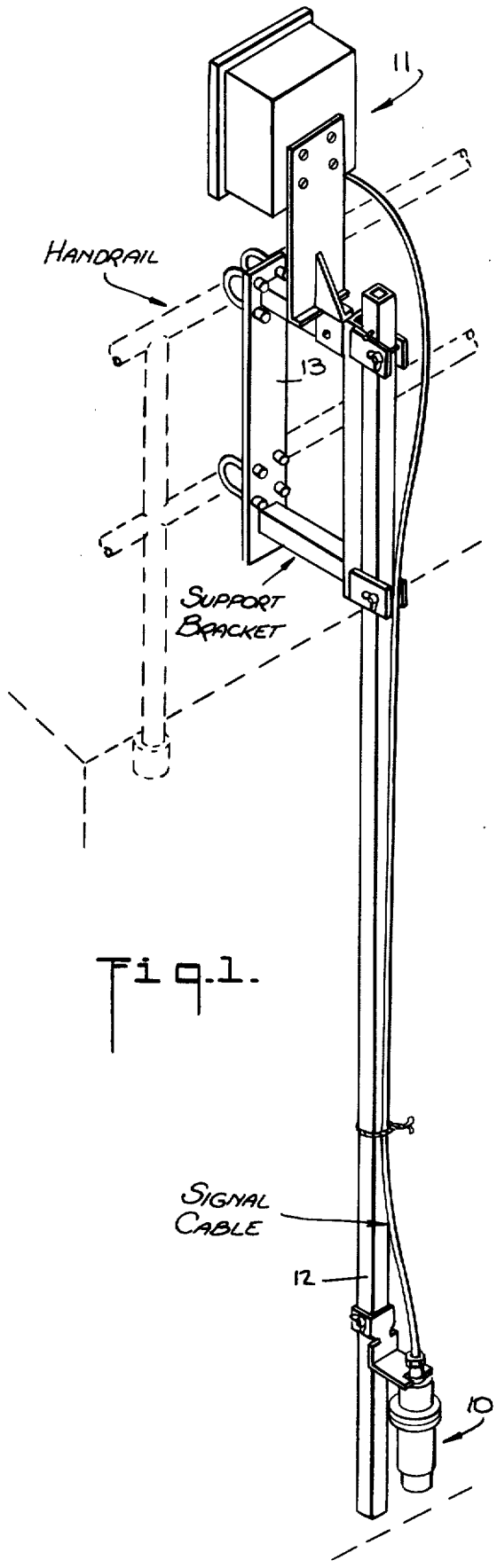
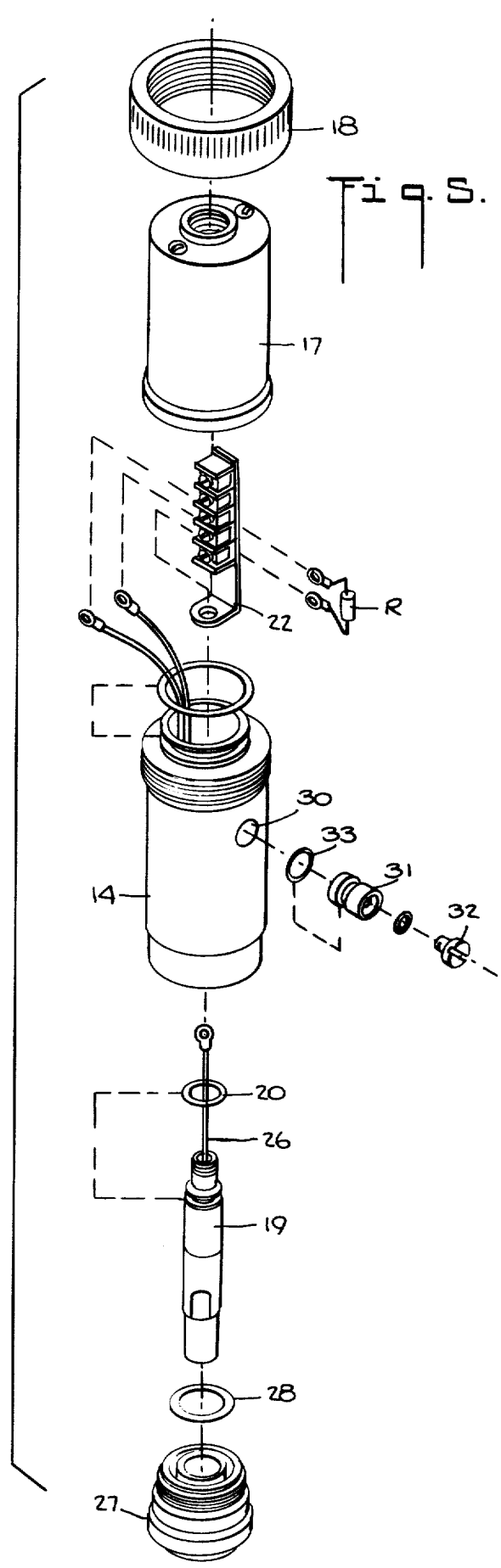

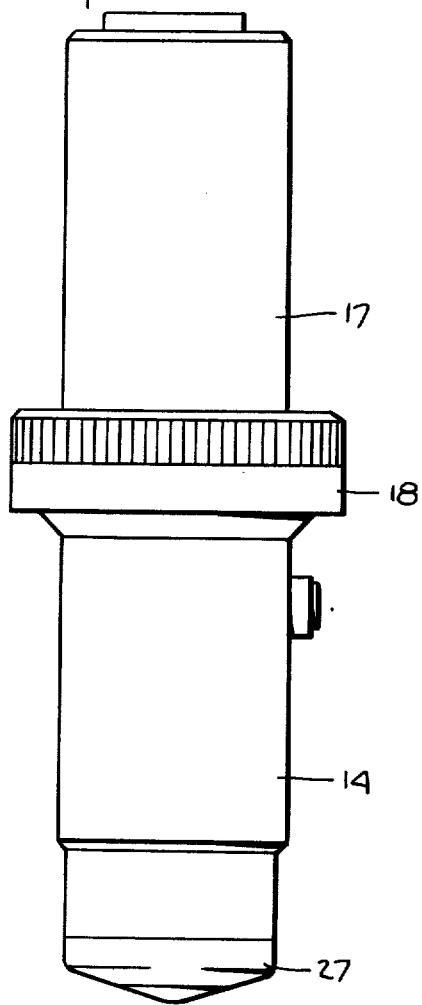
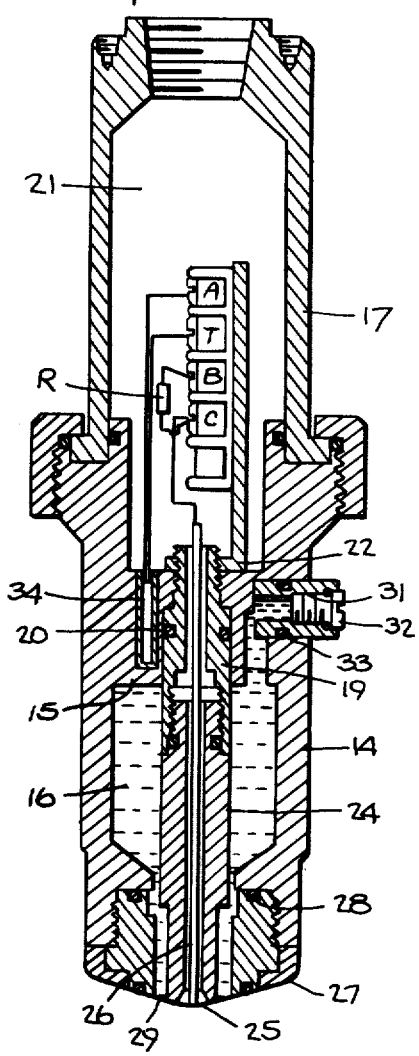
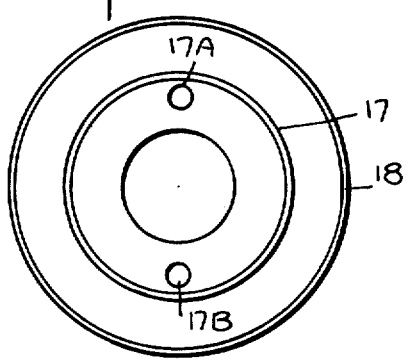
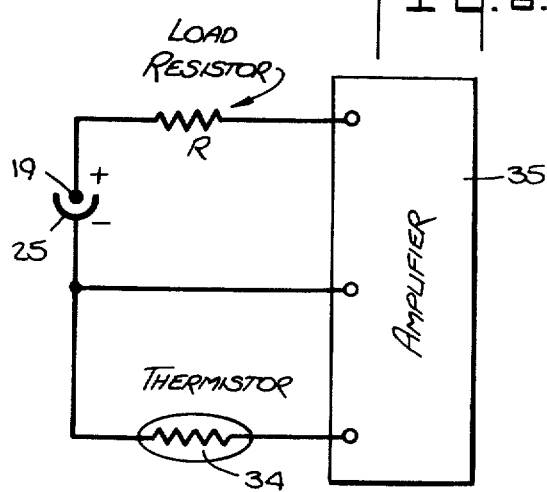

CHLORINE DIOXIDE ANALYZER

BACKGROUND OF INVENTION

This invention relates generally to the disinfection of water by chlorine dioxide, and more particularly to a system adapted to continuously monitor or analyze the concentration of chlorine dioxide dissolved in water used in industrial process solutions, municipal water supplies and in other applications requiring disinfected water, the system including a sensor immersed in the liquid to afford an in situ analysis thereof.

The virtues of chlorination techniques for disinfecting water supplies has long been recognized, but only in recent years hve the hazards involved come to public attention. Thus in studies conducted on the chlorinated water supplies of the city of New Orleans, it was found that the levels of chlorination were such as to release carcinogenic agents dangerous to the community.

The results of this study appear in an article by R. A. Harris, "The Implication of Cancer Causing Substances in Mississippi River Waters" published Nov. 6, 1974 by the Environmental Defense Fund, Washington, D.C. Also relevant in this regard is the article of A. A. Stevens et al., "Chlorination of Organics in Drinking Water," Proceedings of the Conference on the Environmental Impact of Water Chlorination—Oak Ridge National Laboratory, Oak Ridge, Tennessee, Oct. 22-24, 1975 (Journal AWWA 68:615-1976).

Chlorination has been found to result in the formation of chlorinated organic compounds—trihalomethanes. Analytical studies of source and finished waters have demonstrated that trihalomethanes are widespread and arise as a direct result of the chlorination practice. It has also been shown that the organic precursors to trihalomethane formation are the natural humic materials present in almost all source waters.

The disinfection of water with chlorine dioxide rather than chlorine in order to circumvent the formation of trihalomethane carcinogens is now well known. Chlorine dioxide does not produce trihalomethanes in water treated thereby. Moreover, it reacts to reduce the concentration of the precursor such that if chlorine is also used as a disinfectant, the resulting trihalomethane produced is diminished.

Chlorine dioxide gas has a greenish yellow color similar to chlorine gas, but is more toxic. Because of its explosiveness, chlorine dioxide is generally used as a disinfectant in a non-hazardous aqueous solution, for it is extremely soluble in water, about five times more so than chlorine.

The main concern of the present invention is with the continuous monitoring or analysis of chlorine dioxide dissolved in water. In any municipal, industrial, or other process which makes use of this disinfectant, it is vital that the concentration of the solution be accurately determined in order to effect proper regulation of the amount of chlorine dioxide introduced into the process. Thus in an automatic control system for governing a process making use of chlorine dioxide dissolved in a process liquid, one must be able to continuously sense the existing concentration of the dissolved chlorine dioxide (DCD) in order to compare this process variable with a set point to generate a control signal for regulating the process.

Presently known procedures for the continuous analysis of chlorine dioxide concentrations leave much to be desired. Existing analytical techniques described in the chemical literature are either batch procedures which are unsuitable for automatic process control or involve flow-through optical procedures employing spectrophotometry.

The problem of chlorine dioxide analysis is complicated by the presence in most waters of residual chlorine (free and combined) and chlorite as well as chlorine dioxide. Since chlorine dioxide reacts in a manner similar to chlorine with reagent chemicals, with conventional analytic techniques, one cannot differentiate between these distinctly different disinfectant agents.

A widely used technique to overcome this problem is the method described by Haller et al. in Anal. Chem. 31, 872 (1948) in which penylarsene oxide is used as a titrant for the determination of free chlorine, combined chlorine, chlorite and chlorine dioxide in any combination. But this technique is time-consuming and difficult to carry out.

The spectrophotometric approach lends itself to continuous analysis but is subject to serious error caused by contamination of the optical windows. And because at low levels of DCD concentrations, color-developing reagents must be added to enhance the sensitivity of the optical analyzer, this dictates the inclusion of microflow pumps to deliver the reagent. The need to maintain these pumps as well as to replenish the reagents which are consumed in the course of testing represent practical drawbacks.

Inasmuch as the present invention makes use of a DCD sensor which is structurally similar to the dissolved oxygen probe disclosed in the Poole U.S. Pat. No. 3,948,746, this patent is made of record herein even though the Poole probe is incapable of analyzing dissolved chlorine dioxide, for the diffusion membrane incorporated in this probe is not permeable to chlorine dioxide.

SUMMARY OF INVENTION

In view of the foregoing, the main object of this invention is to provide a system adapted to continuously and accurately analyze the concentration of chlorine dioxide dissolved in a liquid, the system including a DCD sensor immersible in the liquid to afford an in situ analysis thereof.

More particularly, an object of this invention is to provide a sensor of the above-noted type which incorporates an electrochemical cell adapted to separate chorine dioxide from the liquid in which it is dissolved, and to generate an output current proportional to the concentration of the chlorine dioxide.

Yet another object of the invention is to provide an electrochemical cell whose electrodes remain clean and functional even after prolonged operation, and whose electrolyte is not consumed and therefore need not be replenished.

Also an object of this invention is to provide a sensor including a temperature-responsive element to correct the readings for changes in the temperature of the liquid being tested.

Briefly stated, in a system in accordance with the invention for continuously and accurately measuring the concentration of chlorine dioxide dissolved in water, a sensor is provided which is immersed in the water being tested to produce a current signal which is a function of DCD concentration, which signal is convertible to an output signal that may be indicated or recorded, or applied to an automatic process control system to regulate the DCD concentration. The sensor includes an insulating casing having an electrolyte chamber filled with a halide salt electrolyte solution.

The mouth of the chamber which is exposed to the water being tested is covered by a diffusion membrane assembly provided with a hydrophobic diffusion membrane. This membrane is permeable to chlorine dioxide but impermeable to water, whereby chlorine dioxide dissolved in the water diffuses through the membrane into the electrolyte to react therewith.

Disposed within the electrolyte chamber is an electrode assembly including a noble-metal measuring electrode and an oxidizable-metal counter electrode. These electrodes are bridged by the electrolyte, whereby in the absence of DCD, the measuring electrode becomes negatively polarized to inhibit the flow of electrons thereto, and the counter electrode becomes positively charged, whereas in the presence of DCD the measuring electrode becomes partially depolarized and accepts electrons produced by oxidation of the counter electrode, the resultant flow of current being a function of the amount of chlorine dioxide admitted into the cell.

To prevent the build-up of an oxide layer on the counter-electrode, the electrolyte includes a complexing agent which complexes ions of the counter electrode material to maintain this electrode clean and functional.

OUTLINE OF DRAWINGS

For a better understanding of the invention as well as other objects and further features thereof, reference is made to the following detailed description to be read in conjunction with the accompanying drawings, wherein:

FIG. 1 illustrates an actual installation of a system in accordance with the invention for the in situ analysis of chlorine dioxide dissolved in a liquid;

FIG. 2 is an elevation of the sensor included in the system;

FIG. 3 is a plan view of the sensor;

FIG. 4 is a section taken through the longitudinal axis of the sensor;

FIG. 5 is an exploded view of the sensor; and

FIG. 6 shows the circuit arrangement of the electrochemical cell and the thermistor included in the sensor.

DESCRIPTION OF INVENTION

A DCD measuring system in accordance with the invention is constituted, as shown in FIG. 1, by a DCD sensor 10 and a transmitter 11 electrically coupled thereto, the system functioning to continuously measure and indicate the DCD concentration in a process stream or tank. Thus where the sensor is immersed in a tank containing a liquid to be tested, the sensor is supported on the lower end of a beam 12 whose other end is secured to a bracket 13 on which transmitter 11 is mounted. The bracket is anchored on a hand rail 13 along the edge of the tank.

Sensor 10 includes an amperometric-electrochemical cell which acts to generate a current signal compensated for changes in the process liquid temperature. The circuits of the transmitter, which may be conventional and form no part of the present invention, function to receive the current signal yielded by the sensor and to convert it into a proportional 4 to 20 mAdc output signal. This output signal may be conveyed to compatible secondary instrumentation adapted to indicate or record the DCD concentration or to automatically control the DCD concentration in the process liquid. In its most elementary form, as in a situation in which all that is required is a continuous reading of DCD concentration, the sensor may simply be coupled to a suitable indicator-circuit responsive to the current flowing through the cell.

Sensor 10, as shown in FIGS. 2 to 5, includes a cell sensitive only to DCD disposed within a hollow cylindrical casing 14 fabricated of a suitable electrical insulation material of good structural strength, such as polyvinyl chloride or polycarbonate. Formed adjacent the upper end of the casing is a constriction 15 of reduced internal diameter that effectively divides the interior of the sensor into a lower electrolytic chamber 16 and an upper terminal chamber 21 which is completed by a cylindrical cap 17 removably coupled to the casing by a coupling nut 18. Cap 17, as shown in FIG. 3, is provided with threaded holes 17A and 17B at its upper end to facilitate mounting of the sensor.

Suspended coaxially within electrolytic chamber 16 is an electrode assembly whose upper section is formed by a tubular counter electrode or anode 19 fabricated of copper, silver or other suitable oxidizable metal. The upper end of anode 19 is threaded and projects through constriction 15 into the terminal chamber 21, an O-ring 20 being provided on this end to prevent leakage of electrolyte from electrolyte chamber 16 into the terminal chamber.

Attached to the threaded end of anode 19 is the foot of an L-shaped conductive bracket 22 whose leg extends upwardly into terminal chamber 21 to support therein a terminal contact strip 23, one of whose contacts is connected to bracket 22 to provide a grounded terminal for anode 19.

The electrode assembly disposed coaxially within electrolyte chamber 16 further includes an insulating tubular stem 24 whose upper end is socketed within the lower end of anode 19. A button-shaped measuring electrode or cathode 25 is fitted into the tip of stem 24. This electrode, which is formed of a noble metal such as gold or platinum, is connected by a lead 26 extending through stem 24 and anode 19 of the electrode assembly into terminal chamber 21 where it is connected to terminal C. This terminal is also connected to terminal B of the contact strip through a load resistor R.

The open mouth of electrolyte chamber 16 which is exposed to the liquid being tested is closed by a removable membrane assembly formed by a cap 27 having a central bore therein, the cap being threadably received in the lower end of casing 14, an O-ring 28 providing the necessary seal therebetween. Stretched across the face of a cap 27 is a diffusion membrane 29 which is permeable only to chlorine dioxide, the membrane otherwise constituting a hydrophobic barrier between the electrolyte chamber and the water in which the sensor is immersed, so that only the gas filters into the electrolytic chamber.

The gas-permeable membrane is preferably fabricated of Celgard 4510 material made by the Celanese Corporation, this material being a microporous polypropylene fabric of one mil thickness having a pore diameter of 0.04 microns, which fabric is laminated to a non-woven reinforcing polypropylene mesh.

Also usable for the same purpose is General Electric's Mem-213, a hydrophobic membrane which has been found to be permeable to chlorine dioxide. This membrane is a silicone-polycarbonate film (dimethyl silicone/biphenyl a-polycarbonate copolymer). Because the film is relatively delicate and subject to deformation by liquid pressure, it is desirable to design the membrane assembly so as to support the membrane in a manner minimizing such deformation.

A fill hole 30 is bored into casing 14. Inserted therein is a removable plug 31 provided with a set screw 32, the plug 31 being sealed in the fill hole by an O-ring 33. Fill hole 30 communicates with electrolyte chamber 16 and makes it possible to fill this chamber with a suitable electrolyte solution of such salts as KCl, KBr, KI or other halides in combination with EDTA, CDTA, NTA, sodium acetate or other appropriate complexing and buffering agents to buffer the solution at pH 4, 7 or other values.

Also included in the sensor is a thermistor 34 which is embedded in casing 14 and is connected between terminals A and T, the resistance of the thermistor being caused to vary as a function of the temperature of the liquid in which the sensor is immersed.

Principle of Sensor Operation

Sensor 10 acts as an electrochemical cell that generates a current whose magnitude is proportional to the amount of chlorine dioxide dissolved in the liquid being tested. In the following analysis, we shall assume that the measuring electrode in the electrolytic chamber is of gold and the counter electrode is of copper; although, as pointed out above, other noble and oxidizable metals may be used for the anode and cathode, respectively.

We shall further assume that the electrolyte solution is formulated by dissolving 0.1 mole of potassium bromide and 0.1 mole disodium EDTA in one liter of water, and that the pH of the solution is adjusted to pH 7 by means of a sodium hydroxide solution before effecting dilution of the electrolyte in a liter of water. As pointed out previously, other electrolytic solutions are workable within the purview of the invention.

The purpose of the electrolyte is threefold. First, it affords a solution path bridging the anode and cathode electrodes. Second, it complexes ions which are generated by the electrode reactions. Third, it contains a reactant species which interacts with the chlorine dioxide introduced into the electrochemical cell.

The cell responds to the chlorine dioxide diffused therein through the hydrophobic membrane to generate a current whose intensity varies linearly in accordance with changes in the amount of chlorine dioxide dissolved in the liquid being tested. The behavior of the electrochemical cell in the absence or presence of chlorine dioxide is as follows:

A. When chlorine dioxide is absent in the liquid being tested, the gold measuring electrode (cathode 25) becomes negatively-charged while the copper counter electrode (anode 19) becomes positively-charged. Such charging is due to the relative positions of these metals in the electromotive series. The abundance of electrons on the measuring electrode polarizes this electrode and prevents more electrons from flowing toward it; hence no current flows through the cell when chlorine dioxide is absent.

B. When chlorine dioxide is present in the liquid being tested and diffuses into the cell through permeable membrane 29, this gas reacts with the potassium bromide in the electrolyte to produce hypobromous acid:

$$2ClO_2 + Br^- + H_2O \rightarrow HOBr + 2ClO_2^- + H^+ \quad (1)$$
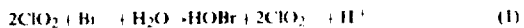

The hypobromous acid produced by reaction (1) reacts at gold measuring electrode 25 in the following manner:

$$HOBr + H^+ + 2e^- \rightarrow H_2O + Br^- \quad (2)$$

As a consequence of reaction (2), measuring electrode 25 is partially depolarized, thereby allowing more electrons to flow towards it. The copper counter-electrode 19 is concurrently oxidized to generate these electrons in accordance with the following reaction:

$$Cu^\circ \rightarrow Cu^{+2} + 2e^- \quad (3)$$

It is important to note that potassium bromide is not consumed in these reactions and therefore need not be replenished. The overall reaction may be expressed as follows:

$$Cu^\circ + 2ClO_2 \rightarrow Cu^{+2} + 2ClO_2^- \quad (4)$$

In order to prevent a layer of oxidized copper from building up on the surface of the copper counter-electrode and inhibiting the flow of current, the EDTA constituent in the electrolyte functions to complex copper ions, thereby keeping this electrode clean and functional. This reaction takes the following form:

$$Cu^{+2} + EDTA^{-4} \rightarrow Cu\,EDTA^{-2} \quad (5)$$
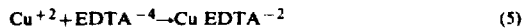

We shall now consider other electrolyte formulations and the resultant reactions. Thus one may substitute potassium iodide for potassium bromide, in which case reactions (1) and (2) above take the form of reactions (6) and (7), respectively:

$$2I^- + 2ClO_2 \rightarrow I_2 + 2ClO_2^- \quad (6)$$

$$2e^- + I_2 \rightarrow 2I^- \quad (7)$$

In the presence of an inert salt such as potassium chloride, the chlorine dioxide then reacts directly at the measuring electrode in the following manner:

$$ClO_2 + e^- \rightarrow ClO_2^- \quad (8)$$

The above reactions result when employing a copper counter electrode. If instead of copper one uses silver as the counter electrode, the following reaction takes place:

$$Ag^\circ \rightarrow Ag^{+1} + e^- \quad (9)$$

In summary, the following modes of reaction are possible:

Reaction Mode I (KBr or KI catalyzed - Cu counter electrode)

$$2ClO_2 + Cu^\circ + EDTA^{-4} \xrightarrow[\text{or}]{.1\,M\,KBr}_{.1\,M\,KI} 2ClO_2^- + CuEDTA^{-2}$$
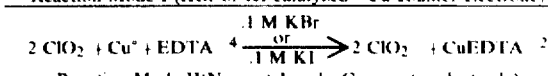

Reaction Mode II (Non-catalyzed - Cu counter electrode)

$$2ClO_2 + Cu^\circ + EDTA^{-4} \xrightarrow{.1M\,KCl} 2ClO_2^- + CuEDTA^{-2}$$

Reaction Mode III (KBr or KI catalyzed - Ag counter electrode)

$$ClO_2 + Ag^\circ + EDTA^{-4} \xrightarrow[\text{.1M KI}]{.1M\,KBr\,or} ClO_2^- + AgEDTA^{-3}$$
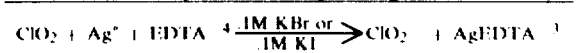

Reaction Mode IV (Non-Catalyzed - Ag counter electrode)

$$ClO_2 + Ag^\circ + EDTA^{-4} \xrightarrow{.1\,M\,KCl} ClO_2^- + AgEDTA^{-3}$$

Regardless of the selected reaction mode, depolarization of the measuring electrodes gives rise to the flow of electrical current whose intensity is directly proportional to the concentration of chlorine dioxide in the liquid being tested. This current may be amplified or otherwise conditioned to produce an output signal by suitable secondary instrumentation.

The electrochemical cell also lends itself to two amperometric modes of operation—namely, the galvanic mode in which the cell itself generates the current as a function of the chlorine dioxide concentration, and the impressed potential mode in which a voltage is applied across the electrodes to produce a current flow in the cell as a function of chlorine dioxide concentration.

Reaction Mode I is preferably carried out in the impressed potential amperometric mode to cause the cell to function in a current region in which dissolved oxygen in the liquid being tested offers no interference. On the other hand, Reaction mode III can be performed in the galvanic amperometric mode, for no impressed potential is required to avoid interference from dissolved oxygen.

Since membrane 29 is permeable to chlorine dioxide and impermeable to water, only un-ionized species are detected, thereby eliminating interferents such as $MnO_4^-$, $ClO^-$, $ClO_2^-$ and $ClO_3^-$ which may be encountered in the water being tested. By proper choice of the electrode-electrolyte-membrane combination which constitute an electrochemical cell in accordance with the invention, interference from HOCl and chloramines may be reduced to minimal level.

Temperature Compensation

Referring now to FIG. 6, the circuit arrangement of an amperometric cell formed by anode 19, cathode 29 and the electrolyte path bridging these electrodes in conjunction with thermistor 34 will now be explained. Thermistor 34 serves as a temperature-sensitive variable resistor in a feedback voltage path in an amplifier 35 whose input is coupled to the cell electrodes through load resistor R.

Load resistor R functions to provide a small but necessary load for the sensor whose current output is fed via a suitable cable connector to an amplifier 35 included in transmitter 11. Amplifier 35 operates to convert the current yielded by the cell to a useful temperature-compensated electronic output signal whose value depends solely on the DCD concentration and may therefore be used to provide an accurate and continuous reading thereof.

While there has been shown and described a preferred embodiment of a chlorine dioxide analyzer in accordance with the invention, it will be appreciated that many changes and modifications may be made therein without, however, departing from the essential spirit thereof.

I claim:

1. A system adapted to continuously and accurately measure the concentration of chlorine dioxide dissolved in water which also has oxygen dissolved therein, the system being provided with a sensor immersed in the water being tested to afford in situ measurements, said sensor comprising:

(A) an insulating casing having an electrolyte chamber therein whose open mouth is exposed to the water being tested, said chamber being filled with an electrolyte constituted by a halide salt in a water solution;

(B) a membrane assembly covering the mouth of the chamber to isolate the chamber from the water, said assembly being provided with a hydrophobic diffusing membrane permeable to chlorine dioxide and impermeable to water whereby chlorine dioxide dissolved in the water diffuses through the membrane to enter into said chamber and react with said electrolyte;

(C) an electrode assembly disposed within said chamber, said assembly including a noble-metal measuring electrode and an oxidizable-metal counter electrode, said electrodes being bridged by the electrolyte to define an electrochemical cell which in the absence of chlorine dioxide produce a reaction causing the measuring electrode to become negatively polarized and the counter electrode to become positively charged and which in the presence of chlorine dioxide produces a reaction causing the measuring electrode to become partially depolarized to render it receptive to electrons resulting from the oxidation of the counter electrode whereby the resultant current flow has an intensity depending on the concentration of the chlorine dioxide, said noble-metal being selected from a class consisting of gold and platinum and the oxidizable metal being selected from a class consisting of copper and silver, said electrolyte including a complexing agent to react with ions produced by the counter electrode to inhibit the build-up of an oxide layer thereon, thereby maintaining said counter electrode clean and functional; and (D) means to impress a potential across said electrodes causing said cell to function in a current region in which dissolved oxygen in the water being tested offers no interference with said current flow as a function of chloride dioxide concentrations.

2. A sensor as set forth in claim 1, wherein said complexing agent is EDTA.

3. A sensor as set forth in claim 1, wherein said electrolyte includes a buffering agent to maintain said electrolyte at a predetermined pH.

4. A sensor as set forth in claim 1, wherein said halide salt is potassium bromide.

5. A sensor as set forth in claim 1, wherein said halide salt is potassium chloride.

6. A sensor as set forth in claim 1, wherein said halide salt is potassium iodide.

7. A sensor as set forth in claim 1, wherein said membrane is formed by a microporous polypropylene fabric.

8. A sensor as set forth in claim 7, wherein said fabric has pores of about 0.04 micron size.

9. A sensor as set forth in claim 1, wherein said membrane is formed by a silicone-polycarbonate film.

* * * * *